United States Patent [19]

Summers, Jr.

[11] Patent Number: 4,605,669

[45] Date of Patent: Aug. 12, 1986

[54] LIPOXYGENASE INHIBITING NAPHTHOHYDROXAMIC ACIDS

[75] Inventor: James B. Summers, Jr., Libertyville, Ill.

[73] Assignee: Abbott Laboratories, North Chicago, Ill.

[21] Appl. No.: 727,464

[22] Filed: Apr. 26, 1985

[51] Int. Cl.[4] ............... A61K 31/185; A61K 31/205; C07C 83/10
[52] U.S. Cl. .................. 514/575; 260/500.5 H; 260/501.1; 260/501.11; 514/555
[58] Field of Search ............ 260/500.5 H, 501.1, 260/501.11; 514/575, 555

[56] References Cited

U.S. PATENT DOCUMENTS

| | | | |
|---|---|---|---|
| 2,397,508 | 4/1946 | Rousalt et al. | 260/500.5 H |
| 3,819,702 | 6/1974 | Lafon | 260/500.5 H |
| 3,900,514 | 8/1975 | Chappelow et al. | 260/500.5 H |
| 3,968,145 | 7/1976 | Ghelardoni et al. | 260/500.5 H |
| 3,978,116 | 8/1976 | Fried et al. | 260/500.5 H |
| 4,109,013 | 8/1978 | Grill et al. | 260/500.5 H |

FOREIGN PATENT DOCUMENTS 1548641  10/1968  France ............ 260/500.5 H

*Primary Examiner*—J. E. Evans
*Attorney, Agent, or Firm*—Michael J. Roth; Martin L. Katz

[57] ABSTRACT

Compounds of the formula

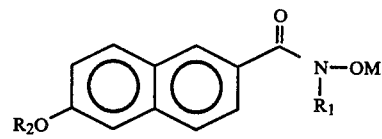

where $R_1$ is H, or $C_1$ to $C_6$ alkyl; $R_2$ is selected from $C_1$ to $C_{22}$ alkyl, cycloalkyl, aralky or alkenyl; and M is a pharmaceutically acceptable cation, are potent inhibitors of the enzymes 5-, 12- and 15-lipoxygenase.

9 Claims, No Drawings

1

LIPOXYGENASE INHIBITING NAPHTHOHYDROXAMIC ACIDS

TECHNICAL FIELD

This invention relates to novel organic compounds which inhibit lipoxygenase enzymes. It also relates to methods of making such compounds, and to methods of inhibiting lipoxygenase enzymes in human and animal hosts in need of such treatment.

The lipoxygenases are a family of enzymes which catalyze the oxidation of arachidonic acid. The enzyme 5-lipoxygenase converts arachidonic acid to 5-hydroperoxyeicosatetraenoic acid (5-HPETE). This is the first step in the metabolic pathway which yields 5-hydroxyeicosatetraenoic acid (5-HETE) and the leukotrienes (LTs). Similarly, 12- and 15-lipoxygenase convert arachidonic acid to 12- and 15-HPETE, respectively. Biochemical reduction of 12-HPETE leads to 12-HETE, while 15-HETE is the precursor of the class of compounds known as lipoxins.

A variety of biological effects are associated with these products of lipoxygenase activity, and many are implicated as mediators in various disease states. The C4 and D4 LTs are potent constrictors of human bronchial smooth muscle in vitro, and induce bronchoconstriction when administered as aerosols to non-asthmatic human volunteers. LTB4 and 5-HETE are potent chemotactic factors for inflammatory cells such as polymorphonuclear leukocytes. They are also found in the synovial fluid of patients with rheumatoid arthritis. The biological activity of the LTs has been reviewed by Samuelsson, *Angew. Chem. Int. Ed. Eng.*, 21, 902 (1982), and by Green and Lambeth, *Tetrahedron*, 39, 1687 (1983), the disclosures of which are incorporated herein by reference.

The product 12-HETE has been found at high levels in the epidermal tissue of patients with psoriasis. The lipoxins have been shown to stimulate lysozomal enzyme and superoxide ion release from neutrophils.

Thus, lipoxygenase enzymes play an important role in the biosynthesis of mediators of asthma, allergy, arthritis, psoriasis, and inflammation. Blocking these enzymes interrupts the biochemical pathway involved in these disease states.

BACKGROUND ART

Relatively few compounds are known from the prior art which are inhibitors of lipoxygenase enzymes. Among the lipoxygenase inhibitors known to the art are: AA-861, a 5-lipoxygenase inhibitor, disclosed in U.S. Pat. No. 4,393,075, issued July 12, 1983 to Terao et al.; pyrazolo pyridines, which are 5-lipoxygenase inhibitors, disclosed in European patent application of Irikura et al., Ser. No. 121,806, published Oct. 17, 1984; arachidonyl hydroxamic acid, a 5-lipoxygenase inhibitor, disclosed in E. J. Corey et al., *J. Am. Chem. Soc.*, 106, 1503 (1984) and European Patent Application of P. H. Nelson, Ser. No. 104,468, published April 4, 1984; BW755C, inhibitor of 5- and 12-lipoxygenases, disclosed in Radmark et al., *FEBS Lett.*, 110, 213 (1980); nordihydroguaiaretic acid, an inhibitor of 5- and 15-lipoxygenases, disclosed in Morris et al., *Prostaglandins*, 19, 371 (1980); REV-5901, a 5-lipoxygenase inhibitor, disclosed in Coutts, Meeting Abstract 70, *Prostaglandins and Leukotrienes* '84; alkyl quinoline N-oxides, as disclosed in the German application of Kyowa Hakko Kogyo KK, abstracted in Derwent Abstract 884-289705/47, and stated to be useful for the treatment of bronchial asthma, atopic dermatitis, inflammation, edema, hypertension, ischemic brain disease and arteriosclerosis; and benzoxaprofen, disclosed in J. Walker, *Pharm. Pharmacol.*, 31, 778 (1979).

It would be useful to have compounds which are more potent inhibitors of these enzymes. In addition, a number of compounds identified as having some lipoxygenase inhibitory activity are structurally based on highly unsaturated lipid compounds which are derivatives of arachidonic acid. Such compounds are highly susceptible to oxidation in vitro and to breakdown by conventional pathways of lipid metabolism in vivo. Thus, as well as having the desired potency, it would be desirable to have agents which are relatively simple in structure, and relatively resistant to oxidation and metabolism.

It is an object of the present invention to provide compounds which are highly potent inhibitors of lipoxygenase enzymes.

It is another object of this invention to provide compounds having structures which are simpler and more stable than prior art compounds having lipid-like structures.

It is yet another object of this invention to provide compounds which inhibit lipoxygenase activity in vivo.

These and other objects of this invention will be evident from the following disclosure.

DISCLOSURE OF THE INVENTION

The present invention provides compounds of the formula

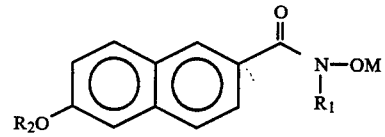

where $R_1$ is H, or $C_1$ to $C_6$ alkyl; $R_2$ is selected from $C_1$ to $C_{22}$ alkyl, cycloalkyl, aralky or alkenyl; and M is a pharmaceutically acceptable cation.

In preferred compounds, $R_1$ is $C_1$ to $C_6$ alkyl, and $R_2$ is $C_2$ to $C_6$ alkyl.

The terms "alkyl", "cycloalkyl" and "alkenyl" are used herein to mean straight and branched chain saturated, cyclic and unsaturated radicals, respectively, including, but not limited to, methyl, ethyl, ethenyl, n-propyl, isopropyl, 2-propenyl, n-butyl, sec-butyl, isobutyl, tert-butyl, 1-, 2-, or 3-butenyl, cyclopropyl, cyclohexyl, ethylcyclohexyl, n-nonyl, 2-ethyl octadecyl, n-eicosyl and the like.

By "aralky" herein is meant a substituted or unsubstituted aromatic ring group appended to an alkyl radical as defined above, including, but not limited to benzyl, alpha- or beta-naphthylmethyl, halobenzyl, nitrobenzyl, alkoxybenzyl, and the like.

The term "pharmaceutically acceptable cation" is used herein to mean hydrogen and the nontoxic cations based on the alkali and alkaline earth metals, such as sodium, lithium, potassium, calcium, magnesium, and the like, as well as those based on nontoxic ammonium, quaternary ammonium, and amine cations, including, but not limited to, ammonium, tetramethylammonium, tetraethylammonium, methylamino, dimethylamino, trimethylamino, triethylamino, and ethylamino cations, and the like.

Method of Treatment

This invention also provides a method of inhibiting 5-, 12- and/or 15-lipoxygenase activity in a human or lower animal host in need of such treatment, which method comprises administration to the human or lower animal host an amount of a compound of this invention effective to inhibit lipoxygenase activity in the host. The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intramuscular, intrathecal, intraarticular, epidural and intraarterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from 0.001 to 100 mg/kg body weight daily and more usually 0.01 to 10 mg/kg/day. Dosage unit compositions may contain such amounts or such submultiples thereof as may be used to make up the daily dose. It will be understood, however, that the specific dose level for any particular patient will depend upon a variety of factors including the activity of the specific compound employed, the age, body weight, general health, sex, diet, time and route of administration, rates of absorption and excretion, combination with other drugs and the severity of the particular disease being treated.

Formulation of Pharmaceutical Compositions

This invention also provides compositions in unit dosage form for the inhibition of 5-, 12- and/or 15-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the compositions of this invention, as available in the pharmaceutical arts. Injectable preparations, such as sterile injectable aqueous or oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile, nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compounds of this invention can be prepared by mixing the drug with suitable nonirritating excipients such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

Synthesis of Compounds

The compounds of this invention are synthesized according to the following scheme. Although the sequence illustrated the synthesis of compounds wherein $R_1$ is H and $R_2$ is methyl, other compounds of the invention can be made by substitution of the appropriate compounds for the indicated starting materials.

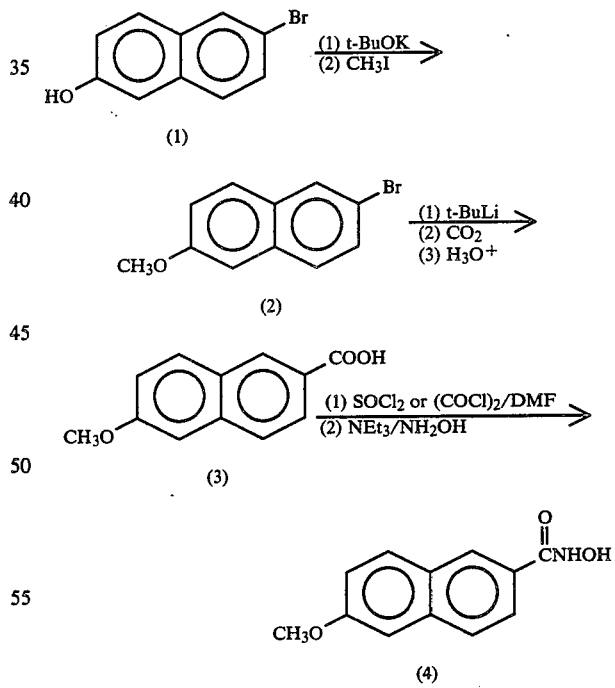

Deprotonation of 6-bromo-2-naphthol (1) with potassium t-butoxide in DMSO followed by alkylation with methyl iodide affords the bromo ether (2). Lithium halogen exchange between this ether and t-butyl lithium, followed by treatment with dry ice and aqueous workup leads to the ether acid (3). This is then converted to the hydroxamic acid (4) by first reacting with either thionyl chloride or oxalyl chloride followed by reaction with hydroxylamine hydrochloride in the presence of triethylamine. A mixture of tetrahydrofuran and water (2:1 v/v) is used as a solvent in the latter reaction.

The following examples further illustrate the synthesis and use of compounds according to this invention.

EXAMPLE 1

6-(1-nonoxy)-2-naphthohydroxamic acid a. 2-bromo-6-(1-nonloxy) naphthalene

Potassium t-butoxide (1.67 g, 14.8 mmol) was added to a solution of 6-bromo-2-naphthol (3.0 g, 13.5 mmol) in DMSO (30 mL). After stirring for 10 minutes, 1-bromononane (3.63 g, 17.5 mmol) was added to the solution. The reaction mixture was stirred for an additional 15 minutes and then was poured into 2N HCl solution (75 mL). Ether (75 mL) was added and the organic phase was washed with 2N NaOH and saturated sodium chloride, dried over $MgSO_4$ and evaporated. The solid residue could be carried on directly or could be purified by flash chromatography on 100 g silica gel using 3% ether in hexanes. Yield was 3.1 g (66%).

NMR (300 MHz, $CDCl_3$): 0.87 (t, 3H, $CH_3$); 1.23-1.55 [m, 12H ($CH_2)_6$]; 1.85 (quin, 2H, $CH_2$); 4.05 (t, 2H, $CH_2O$); 7.07-7.90 (m, 6H, aromatic).

IR: ($CDCl_3$): 2930, 2860, 1660, 1590, 1208.

Mass Spectrum: 348, 350 ($M^+$); 222, 224 ($M^+$—$C_9H_{18}$).

b. 6-(1-nonoxy)-2-naphthoic acid

Tert-butyl lithium (4.4 mL, 1.6 M) was added at $-78°$ C. to a solution of 2-bromo-6-(1-nonyloxy) naphthalene (1.2 g, 3.4 mmol) in THF (40 mL). After stirring 60 minutes at $-78°$ C., the mixture was transferred through a cannula to a 250 mL Erlenmeyer flask containing dry ice (approx. 20 g) covered by anhydrous ether. After the transfer was complete and the mixture had warmed to room temperature, the solution was poured into 2N HCl (75 mL). The organic phase was dried with saturated NaCl solution and $MgSO_4$ and evaporated. The solid residue was sufficiently pure to use directly, but could be recrystallized from aqueous ethanol. Yield was 1.0 g (94%).

NMR (300 MHz, DMSO-$d_6$): 0.87 (t, 3H, $CH_3$); 1.23-1.55 [m, 12H, ($CH_2)_6$]; 1.78 (quin, 2H, $CH_2$); 4.10 (t, 2H, $CH_2O$); 7.20-8.51 (m, 6H, aromatic); 12.9 (vbrs, 1H, OH).

IR (KBr): 1760 (brs, C=O).

Mass Spectrum: 314 ($M^{30}$), 270 ($M^{30}$—$CO_2$), 188 ($M^+$—$C_9H_{18}$), 144 ($M^+$—$C_9H_{18}$—$CO_2$).

c. 6-(1-nonoxy)-2-naphthohydroxamic acid

Oxalyl chloride (825 mg, 5.35 mmol) was added dropwise at 0° C. to a solution of 6-(1-nonyloxy)-2-naphthoic acid (800 mg, 2.54 mmol) and dimethyl formamide (180 mg, 2.54 mmol) in methylene chloride (25 mL). Vigorous gas evolution was observed. After stirring for 30 minutes, the above solution was added at 0° C. to a mixture of hydroxylamine hydrochloride (656 mg, 10.2 mmol) and triethylamine (1.54 g, 15.2 mmol) in THF (40 mL) and water (20 mL). After stirring for 1 hour, the reaction mixture was poured into a 2N HCl solution (50 mL). The organic layer was dried with saturated NaCl solution and $MgSO_4$ and then the solvent was evaporated. The residue was recrystallized from acetone to give a white powder. The yield was 625 mg (76%).

Melting Point: 176°–177° C. (dec).

NMR (300 MHz, DMSO-$d_6$): 0.85 (t, 3H, $CH_3$); 1.2-1.5 [m, 12H, ($CH_2)_6$]; 1.77 (quin, 2H, $CH_2$); (t, 2H, —$OCH_2$); 7.21-8.28 (m, 6H, aromatic); 9.04 (vbrs, 1H, NH); 11.27 (s, 1H, OH).

IR: (KBr): 3100-3500 (vbr, NH, OH); 1640 (br; C=O).

Mass Spectrum: 329 ($M^+$); 297 ($M^+$—NHOH); 285 ($M^+$—$CH_3CH_2CH_2$).

EXAMPLE 2

6-Methoxy-2-naphthohydroxamic acid

This compound was obtained with the procedure of Example 1, but using methyl iodide as a starting material.

Melting Point: 190° C. (dec).

NMR (300 MHz, DMSO-$d_6$): 3.88 (s, 3H, $OCH_3$); 7.2-8.3 (m, 6H, aromatic); 9.05 (brs, 1H, NH); 11.28 (s, 1H, OH).

IR (KBr): 3300 (br, NH); 1690 (s, C=O).

Mass Spectrum: 217 ($M^+$); 185 ($M^+$—NHOH); 157 ($M^+$—CONHOH).

EXAMPLE 3

6-(1-butoxy)-2-naphthohydroxamic acid

This compound was obtained with the procedure of Example 1, but using n-butyl bromide as a starting material.

Melting Point: 184°–185° C., (dec).

NMR (300 MHz, DMSO-$d_6$): 0.96 (t, 3H, $CH_3$); 1.47 (m, 2H, $CH_2$); 1.76 (m, 2H, $CH_2$); 4.11 (t, 2H, $CH_2O$); 7.22-8.28 (m, 6H, aromatic); 9.05 1 (brs, 1H, NH); 11.28 (s, 1H, OH).

IR (KBr): 3300 (br, NH); 1700 (C=O).

Mass Spectrum: 259 ($M^+$), 227 ($M^+$—NHOH).

EXAMPLE 4

N-methyl-6-(1-butoxy)-2-naphthohydroxamic acid

This compound was obtained with the procedure of Example 1, but using n-butyl bromide and N-methyl hydroxylamine.

Melting Point: 137°–138° C.

NMR (300 MHz, DMSO-$d_6$) 0.97 (t, 3H, $CH_3$), 1.48 (m, 2H, $CH_2$); 1.76 (quin, 2H, $CH_2$); 3.27 (s, 3H, $CH_3N$) 4.11 (t, 2H, $CH_2O$); 7.17-8.18 (m, 6H, aromatic).

IR (KBr): 3120 (OH), 1660 (C=O).

Mass Spectrum: 273 ($M^+$), 227 ($M^+$—$NCH_3OH$).

EXAMPLE 5

6-(1-heptoxy)-2-naphthohydroxamic acid

This compound was obtained with the procedure of Example 1, but using n-heptyl bromide as a starting material.

Melting Point: 169°–170° C. (dec).

NMR: (300 MHz, DMSO-$d_6$) 0.87 (t, 3H, $CH_3$); 1.25-1.50 [m, 8H, ($CH_2)_4$]; 1.76 (quin, 2H, $CH_2$); 4.08 (t, 2H, $CH_2O$); 7.17-8.30 (m, 6H, aromatic); 9.03 (brs, 1H, NH); 11.25 (s, 1H, OH).

IR (KBr): 3300 (NH); 1700 (sbr, C=O).

Mass Spectrum: 301 ($M^{30}$); 269 ($M^+$—NHOH).

EXAMPLE 6

6-(1-octoxy)-2-naphthohydroxamic acid

This compound was obtained with the procedure of Example 1, but using n-octyl bromide as a starting material.

Melting point: 170°–171° C. (dec).

NMR (300 MHz, DMSO-d$_6$): 0.87 (t, 3H, CH$_3$); 1.25–2.50 [m, 10H, (CH$_2$)$_5$]; 1.76 (quin, 2H, CH$_2$); 4.10 (t, 2H, CH$_2$O); 7.2–8.3 (m, 6H aromatic); 9.03 (s, 1H, NH); 11.25 (s, 1H, OH).

IR (KBr): 3300 (NH); 1700 (sbr, C=O).

Mass Spectrum: 315 (M+); 283 (M+—NHOH).

EXAMPLE 7

6-(1-prop-2-enoxy)-2-naphthohydroxamic acid

This compound was obtained with the procedure of Example 1, but using allyl bromide as a starting material.

Melting Point: 178°–180° C. (dec).

NMR (300 MHz, DMSO-d$_6$): 4.72 (d, 2H, CH$_2$O); 5.31 (dd, 1H, CH$_2$=); 5.47 (dd, 1 H, CH$_2$=); 6.12 (m, 1H, =CH); 7.27–8.30 (m, 6M, aromatic); 9.07 (brs, 1H, NH); 11.28 (brs, 1H, OH).

IR (KBr): 3300 (NH), 1700 (br, s, C=O).

Mass Spectrum: 243 (M+), 211 (M+—NHOH).

EXAMPLE 8

6-(1-non-2-enoxy)-2-naphthohydroxamic acid

This compound was obtained with the procedure of Example 1, but using 1-bromo-non-2-ene as a starting material.

Melting Point: 166°–167° C. (dec).

NMR (300 MHz, DMSO-d$_6$): 0.85 (t, 3H, CH$_3$); 1.2–1.4 [m, 6H, (CH$_2$)$_3$]; 2.05 (q, 2H, CH$_2$); 2.53 (dt, 2H, CH$_2$); 4.12 (t, 2H, CH$_2$O); 5.50 (m, 2H, vinyl); 7.17–8.27 (m, 6H, aromatic); 9.04 (s, 1H, OH); 11.27 (brs, 1H, NH).

IR (KBr): 3300 (NH), 1700 (C=O).

Mass Spectrum: 327 (M+), 295 (M+—NHOH).

EXAMPLE 9

6-(benzyloxy)-2-naphthohydroxamic acid

This compound was obtained with the procedure of Example 1, but using benzyl chloride as a starting material.

Melting Point: 208°–209° C. (dec).

NMR (300 MHz, DMSO-d$_6$): 5.25 (s, 2H, CH$_2$); 7.27–8.30 (m, 11H, aromatic); 9.05 (s, 1H, OH); 11.29 (s, 1H, NH).

IR (KBr): 3300 (NH); 1695 (C=O).

Mass Spectrum: 293 (M+), 261 (M+—NHOH).

EXAMPLE 10

6-(1-dodecoxy)-2-naphthohydroxamic acid

Melting Point: 171°–172° C., (dec).

NMR (300 MHz, DMSO-d$_6$): 0.87 (t, 3H, CH$_3$); 1.25–1.50 [m, 18H, (CH$_2$)$_9$]; 1.76 (quin, 2H, CH$_2$); 4.10 (t, 2H, CH$_2$O); 7.2–8.3 (m, 6H, aromatic); 9.03 (s, 1H, NH); 11.25 (s, 1H, OH).

IR (KBr): 3300 (NH); 1700 (sbr, C=O).

Mass Spectrum: 371 (M+), 339 (M+—NHOH).

EXAMPLE 11

5-Lipoxygenase IC$_{50}$ Determination

The compounds of this invention are potent inhibitors of 5-, 12- and 15-lipoxygenase. An assay to determine 5-lipoxygenase activity was performed in incubations containing various concentrations of the test compound and the 20,000×G supernatant from 7.5×10$^6$ homogenized RBL-1 cells. Reactions were initiated by the addition of radiolabeled arachidonic acid and terminated by acidification and ether extraction. Reaction products were separated from nonconverted substrate by thin layer chromatography and measured by liquid scintillation spectroscopy. Inhibition of 5-lipoxygenase activity was calculated as the ratio of the amounts of product formed in the presence and absence of inhibitor. IC$_{50}$ values were computed as the 50% intercept from linear regression analysis of percentage inhibition versus log concentration plots. Results for compounds of the foregoing Examples are indicated in Table 1, below.

TABLE 1

| Ex. # | R$_1$ | R$_2$ | IC$_{50}$uM |
|---|---|---|---|
| 1 | H | n-nonyl | 20.0 |
| 2 | H | methyl | 8.0 |
| 3 | H | n-butyl | 2.0 |
| 4 | CH$_3$ | n-butyl | 0.41 |
| 5 | H | n-heptyl | 7.1 |
| 6 | H | n-octyl | 6.5 |
| 7 | H | 2-propenyl | 4.6 |
| 8 | H | 3-nonenyl | 2.9 |
| 9 | H | benzyl | 30.0 |

The inhibitory activities of the compounds of this invention against 12- and 15-lipoxygenase can be determined in the foregoing assay in which 12-lipoxygenase obtained from human platelets, or 15-lipoxygenase obtained from soybean, is substituted for the 5-lipoxygenase-containing cell supernatant fraction. Results of these tests for various of the foregoing compounds are indicated in Table 2.

TABLE 2

| | % Inhibition at Indicated Concentration | | | |
|---|---|---|---|---|
| | 15-lipoxygenase | | 12-lipoxygenase | |
| Ex. # | 100 uM | 10 uM | 100 uM | 10 uM |
| 2 | 44 | 23 | — | — |
| 3 | 51 | 45 | — | — |
| 4 | 74 | 29 | — | — |
| 6 | — | — | 71 | 68 |
| 8 | 70 | 10 | 77 | 74 |

What is claimed is:

1. A compound of the formula

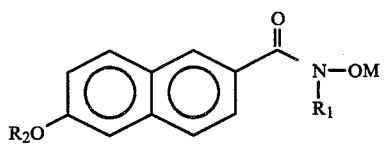

where
R$_1$ is H, or C$_1$ to C$_6$ alkyl;
R$_2$ is selected from C$_1$ to C$_{22}$ alkyl, cycloalkyl, aralcy or alkenyl; and
M is a pharmaceutically acceptable cation.

2. A compound according to claim 1 wherein R$_2$ is C$_2$ to C$_6$ alkyl.

3. A compound according to claim 2 wherein R$_1$ is C$_1$ to C$_6$ alkyl.

4. A compound according to claim 1 wherein the pharmaceutically acceptable cation is a nontoxic cation selected from the group consisting of hydrogen, alkali metal cations, alkaline earth metal cations, and ammonium, quaternary ammonium and amine cations.

5. A method of inhibiting lipoxygenase activity in a human or lower animal host in need of such treatment, comprising administering to the human or lower animal host a compound according to claim 1 in an amount effective to inhibit lipoxygenase activity in the host.

6. A method according to claim 5 wherein the compound is administered orally, parenterally, or topically.

7. A method according to claim 6 wherein the compound is administered at a dosage of from 0.001 to 100 mg/kg body weight per day.

8. A method according to claim 7 wherein the compound is administered at a dosage of from 0.01 to 10 mg/kg body weight per day.

9. A composition in unit dosage form for the inhibition of lipoxygenase activity in a human or lower animal host, comprising a compound according to claim 1 and a pharmaceutical carrier material.

* * * * *